United States Patent [19]

Gozzo et al.

[11] 4,279,927
[45] Jul. 21, 1981

[54] UREAS HAVING INSECTICIDE AND NEMATOCIDE ACTION

[75] Inventors: Franco Gozzo, Saronno; Luigi Abbruzzese; Angelo Longoni, both of Milan, all of Italy

[73] Assignee: Montedison S.p.A., Milan, Italy

[21] Appl. No.: 107,872

[22] Filed: Dec. 28, 1979

Related U.S. Application Data

[62] Division of Ser. No. 860,199, Dec. 13, 1977, abandoned.

[30] Foreign Application Priority Data

Dec. 14, 1976 [IT]  Italy ............................... 30388 A/76

[51] Int. Cl.³ ........................................... A01N 47/28
[52] U.S. Cl. ................................................... 424/322
[58] Field of Search ......................................... 424/322

[56]  References Cited
U.S. PATENT DOCUMENTS 2,723,192  11/1955  Todd ....................................... 71/2.6

FOREIGN PATENT DOCUMENTS 7102615  2/1970  Netherlands .
1232748  7/1971  United Kingdom .

OTHER PUBLICATIONS

Chemical Abstracts 64: 8016f, (1966).
Chemical Abstracts 58: 8885c, (1963).

*Primary Examiner*—Leonard Schenkman

[57]  ABSTRACT

New phenylureas substituted with a polyhaloallyl group and having larvicide activity on lepidoptera, coleoptera, noxious diptera and on nematoda are disclosed. A method for synthesizing the new phenylureas is also disclosed.

23 Claims, No Drawings

UREAS HAVING INSECTICIDE AND NEMATOCIDE ACTION

This is a division of application Ser. No. 860,199, filed Dec. 13, 1977, now abandoned.

THE PRIOR ART

Urea derivatives of the general formula

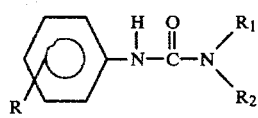

(I)

wherein R often represents 1 or 2 chlorine atoms in position 4 or 3, 4 and $R^1$ and $R^2$ represent two methyl groups or, respectively, a methyl and a methoxyl, have been known for quite some time as inhibitors of phytosynthesis. Thanks to such action these phenylureas are used on a wide scale as herbicides (see for instance F. M. Ashton & A. S. Crafts, "Mode Of Action Of Herbicides"—Wiley-Intersc. Publ. 1973, Chapter 21).

More recently, some researchers of Philips-Duphar, starting from the study of new derivatives of another herbicide, dichlorobenzoyl-(2,6-dichlorobenzonitrile), discovered an interesting larvicide activity in the class of 1-(2,6-dihalobenzoyl)-3-phenyl ureas of the general formula:

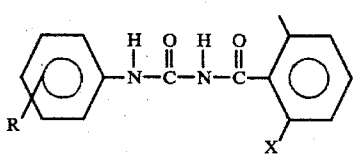

(II)

wherein R represents, in the more active terms, one or two chlorine atoms in position 4 or 3,4 and where X represents a Cl or F atom [see J. van Daalen et al.: in "Naturwissenschaften", 59 (7), 312 (1972)]. Studies carried out on the most active term, commercialized under the name "Dimilin" (R=Cl, X=F), and on its analog (R=3, 4-di Cl, X=Cl), have demonstrated that the most characteristic mode of action of said substituted ureas consists in inhibiting the formation of chitin at the moulting (shedding) of the treated larvae.

However, these latter substituted ureas are obtained by a complicated and expensive synthesis process due to the difficulty of introducing the two halogen atoms into positions 2 and 6 of the benzoyl group.

THE PRESENT INVENTION

One object of this invention is to provide new substituted ureas having a larvicide activity on lepitoptera, coleoptera, noxious diptera and on namatoda which is comparable to, if not superior to, the urea derivatives of formula II and a relatively simple and inexpensive process for synthesizing the same.

This and other objects are accomplished according to this invention which provides phenylureas substituted with a polyhaloallyl group and having the following general formula:

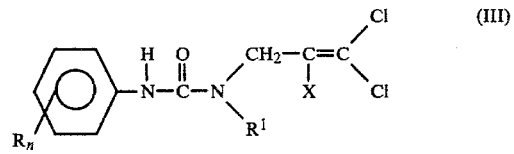

(III)

wherein:
R is H, halogen, $C_1$ to $C_5$ alkyl, $C_1$ to $C_5$ haloalkyl, or polyhaloalkyl with from $C_1$ to $C_5$;
N is 1 or 2;
X is H or Cl;
$R^1$ is H, $C_1$ to $C_5$ alkyl, haloalkyl, polyhaloalkyl from $C_1$ to $C_5$, haloalkenyl, polyhaloalkenyl with from $C_2$ to $C_5$, alkinyl, haloalkinyl, polyhaloalkinyl from $C_2$ to $C_5$, or phenyl.

The synthesis of the compounds of general formula III, which is also an object of this invention, consists in adding a phenylisocyanate to the suitable polyhaloallylamine according to the reaction:

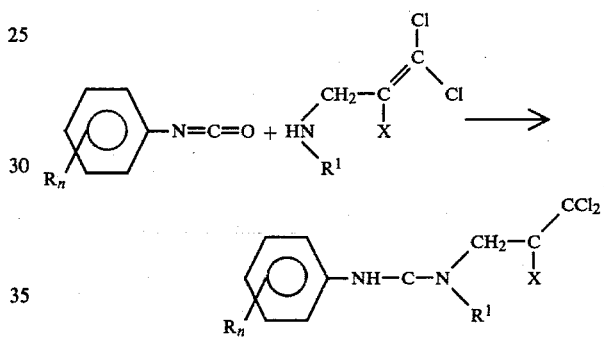

The reaction can be carried out at room temperature and in the presence of solvents.

The N-(3,3-dichloroallyl)-amines or the N-(3,3,2-trichloroallyl)-amines that react with the phenylisocyanate may be prepared by the process described in the Italian patent application No. 28,867 A/76, assigned to Montedison S.p.A.

The substituted ureas of this invention, as already indicated, have an insecticide action on the dipteron larvae, on the coleopteron, lepidopteron and on the nematode larvae.

Although the mechanism according to which the compounds of the invention act on the larvae is not yet known, the observations carried out on the treated species have evidenced a faster action than that observed with "Dimilin" which latter, on the other hand, does not exhibit a nematocide action. Another difference observed between said commercial insecticide and the compounds of the invention consists in the boosted activity observed for the latter on the larvae of a coleopteron, the *Leptinotarsa decemlineata*, when treated under the same conditions (see Table I).

The compounds of the invention act with full effectiveness at concentrations of 0.2 parts per million and higher.

The following examples are given to illustrate the invention in more detail and are not intended to be limiting. The identifying mark number given in the examples is applicants' mark number.

EXAMPLE 1

Preparation of N (3,3-dichloroallyl)-N'(3,4-dichlorophenyl) urea (mark M 7962)

To 0.02 mol of 3,4-dichlorophenylisocyanate, dissolved in 40 ml of ethyl ether, were admixed, at room temperature, 0.02 mol of N-(3,3-dichloroallyl)-amine (prepared starting from 3,3-trichloropropene with hexamethylentetramine—see e.g., Italian patent application No. 28,867 A/76).

The mixture was stirred for about 4 hours, and then, after removal of the solvent, the yellowish solid residue was again diluted with petroleum ether and gathered on a filter. The melting point of this solid residue was comprised between 131° and 132° C.

Theor. Cl=45.17%; theor. C=38.25%; H=2.57%; N=8.92%; Found Cl=43.90%; found C=38.61%; H=2.60%; N=8.80%.

EXAMPLES 2 to 34

Following the same procedure and starting from the appropriate amines, the following ureas were prepared:

-N-methyl-N-(3,3-dichloroallyl)-N'(2-fluorophenyl)urea (applicants' mark M 7635): m.p.=79°-80° C.

| | theoretical = 25.59 |
|---|---|
| Cl% | found = 25.31. |

N-ethyl-N-(3,3-dichloroallyl)-N'(4-chlorophenyl)urea (mark M 8071); m.p.=83°-84° C.:

| Cl% theor. = 34.58 / found = 33.49 | C% theor. = 46.86 / found = 46.80 | H% theor. = 4.26 / found = 4.25 | N% theor. = 9.11 / found = 9.0 |
|---|---|---|---|

N-ethyl-N-(3,3-dichloroallyl)-N'(3,4-dichlorophenyl)urea (mark M7784); m.p.=81°-82° C.:

| Cl% theor. = 41.46 / found = 40.55 | C% theor. = 42.14 / found = 42.21 | H% theor. = 3.54 / found = 3.49 | N% theor. = 8.19 / found = 7.62 |
|---|---|---|---|

N-isopropyl-N-(3,3-dichloroallyl)-N'(2-fluorophenyl)urea (mark M 7860) m.p.=80°-81° C.:

| | theor. = 23.44 |
|---|---|
| Cl% | found = 23.81 |

N-isopropyl-N-(3,3-dichloroallyl)-N'(4-chlorophenyl)urea (mark M 8076); m.p.=105°-106° C.:

| Cl% theor. = 33.07 / found = 33.40 | C% theor. = 48.55 / found = 48.90 | H% theor. = 4.70 / found = 4.71 | N% theor. = 8.71 / found = 8.65 |
|---|---|---|---|

N-isopropyl-N-(3,3-dichloroallyl)-N'(3,4-dichlorophenyl)urea (mark M-7859); m.p.=103°-104° C.:

| Cl theor. = 39.83 / found = 38.93 | C% theor. = 43.85 / found = 44.36 | H% theor. = 3.96 / found = 3.93 | N% theor. = 7.87 / found = 7.74 |
|---|---|---|---|

N-phenyl-N-(3,3-dichloroallyl)-N'(3,4-dichlorophenyl)urea (mark M 7857) m.p.=82°-83° C.:

| Cl% theor. = 36.36 / found = 35.27 | C% theor. = 49.26 / found = 50.77 | H% theor. = 3.10 / found = 3.24 | N% theor. = 7.18 / found = 7.00 |
|---|---|---|---|

N-allyl-N-(3,3-dichloroallyl)-N'-(4-chlorophenyl)urea (mark M 8079); m.p.=82°-83° C.

| Cl% theor. = 33.28 / found = 32.10 | C% theor. = 48.85 / found = 48.82 | H% theor. = 4.10 / found = 4.08 | N% theor. = 8.76 / found = 8.77 |
|---|---|---|---|

N-allyl-N-(3,3-dichloroallyl)-N'(3,4-dichlorophenyl)urea (mark M 7718); m.p.=70°-71° C.

| Cl% theor. = 40.06 / found = 38.68 | C% theor. = 44.10 / found = 44.08 | H% theor. = 3.42 / found = 3.35 | N% theor. = 7.91 / found = 7.61 |
|---|---|---|---|

N-propargyl-N-(3,3-dichloroallyl)-N'phenylurea (mark M 7644) melt point (m.p.)=69°-70° C.

Cl% { theor. = 25.05 / found = 24.30 }  C% { theor. = 55.14 / found = 54.52 }  H% { theor. = 4.27 / found = 4.15 }  N% { theor. = 9.89 / found = 9.75. }

N-propagyl-N-(3,3-dichloroallyl)-N'-(3,4-dichlorophenyl)urea (mark M 7719); m.p.=65°-66° C.

Cl% { theor. = 40.29 / found = 37.33 }  C% { theor. = 44.35 / found = 43.76 }  H% { theor. = 2.86 / found = 2.76 }  N% { theor. = 7.96 / found = 7.58. }

N-allyl-N-(3,3-dichloroallyl)-N'-(m-chlorophenyl)urea (mark M 8078); m.p.=66°-67° C.

Cl% { theor. = 33.28 / found = 31.82 }  C% { theor. = 48.85 / found = 48.37 }  H% { theor. = 4.10 / found = 4.01 }  N% { theor. = 8.76 / found = 8.61. }

N-propargyl-N-(3,3-dichloroallyl)-N'-(m-chlorophenyl)urea (mark M 8206); m.p.=108°-109° C.

Cl% { theor. = 33.49 / found = 33.12 }  C% { theor. = 49.16 / found = 48.90 }  H% { theor. = 3.49 / found = 3.46 }  N% { theor. = 8.82 / found = 8.79. }

N-(3,3-dichloroallyl)-N'-(1,1-dimethylpropargyl)-N'-(p-chlorophenyl)urea (mark M 8273); m.p.=105°-106° C.

Cl% { theor. = 23.54 / found = 22.95 }  C% { theor. = 55.82 / found = 56.19 }  H% { theor. = 6.02 / found = 6.12 }  N% { theor. = 9.36 / found = 9.07. }

N-(1,1-dimethylpropargyl)-N-(3,3-dichloroallyl)-N'-(3,4-dichlorophenyl)urea (mark M 8216); m.p.=79°-80° C.

Cl% { theor. = 47.39 / found = 49.19 }  H% { theor. = 3.71 / found = 4.33 }  N% { theor. = 7.36 / found = 7.93. }

N-allyl-N-(3,3-dichloroallyl)-N'-(2-trifluoromethylphenyl)urea (mark M 7723); m.p.=47°-48° C.

Cl% { theor. = 20.07

-continued found = 19.88.

Cl% { theor. = 23.70 / found = 23.11 }  C% { theor. = 56.20 / found = 56.18 }  H% { theor. = 5.39 / found = 5.41 }  N% { theor. = 9.36 / found = 9.16. }

N-allyl-N-(3,3-dichloroallyl)-N'-(m-methylphenyl)urea (mark M 7721); m.p.=79°-80° C.

N-ethyl-N-(3,3-dichloroallyl)-N'-(p-ethylphenyl)urea (mark M 8434); m.p.=67°-68° C.

Cl% { theor. = 30.78 / found = 30.71 }  C% { theor. = 52.12 / found = 51.87 }  H% { theor. = 4.37 / found = 8.01 }  N% { theor. = 8.10 / found = 8.01. }

N-isopropyl-N-(3,3-dichloroallyl)-N'-(p-ethylphenyl)urea (mark M 8435); m.p.=82°-83° C.

Cl% { theor. = 22.49 / found = 22.58 }  C% { theor. = 57.15 / found = 57.64 }  H% { theor. = 6.39 / found = 6.52 }  N% { theor. = 8.88 / found = 8.89. }

N-(2,3-dichloroallyl)-N'-(4-ethylphenyl)urea (mark M 8455); m.p.=97°-98° C.:

Cl% { theor. = 25.95 / found = 24.37 }  N% { theor. = 10.25 / found = 10.97. }

N-allyl-N-(3,3-dichloroallyl)-N'-(4-ethylphenyl)urea (mark M 8454); m.p.=53°–54° C.:

| Cl% | theor. = 22.63 | C% | theor. = 57.52 | H% | theor. = 5.79 | N% | theor. = 8.94 |
|---|---|---|---|---|---|---|---|
| | found = 22.50 | | found = 56.96 | | found = 5.75 | | found = 8.45. |

N-methyl-N-(3,3,2-trichloroallyl)-N'(p-chlorophenyl) urea (mark M 8074); m.p.=104°–105° C.:

| Cl% | theor. = 43.23 | C% | theor. = 40.28 | H% | theor. = 3.07 | N% | theor. = 8.54 |
|---|---|---|---|---|---|---|---|
| | found = 41.85 | | found = 40.37 | | found = 3.05 | | found = 8.41. |

N-propargyl-N-(3,3,2-trichloroallyl)-N'-(3,4-dichlorophenyl)urea (mark M 8275); m.p.=97°–98° C.:

| Cl% | theor. = 45.85 | C% | theor. = 40.40 | H% | theor. = 2.35 | N% | theor. = 7.25 |
|---|---|---|---|---|---|---|---|
| | found = 46.62 | | found = 41.35 | | found = 2.39 | | found = 7.29. |

N-propargyl-N-(3,3,2-trichloroallyl)-N'-(p-chlorophenyl)urea (mark M 8276); m.p.=100°–101° C.:

| Cl% | theor. = 40.29 | C% | theor. = 44.35 | H% | theor. = 2.86 | N% | theor. = 7.96 |
|---|---|---|---|---|---|---|---|
| | found = 39.46 | | found = 44.52 | | found = 2.90 | | found = 7.92. |

N-propargyl-N-(3,3,2-trichloroallyl)-N'-(m-chlorophenyl)urea (mark M 8278); m.p.=81°–82° C.:

| Cl% | theor. = 44.35 | H% | theor. = 2.86 | N% | theor. = 7.96 |
|---|---|---|---|---|---|
| | found = 45.22 | | found = 2.93 | | found = 8.09. |

N-(1,1-dimethylpropargyl)-N-(3,3,2-trichloroallyl)-N'-(3,4-dichlorophenyl)urea (mark M 8427); m.p.=101°–102°:

| Cl% | theor. = 42.76 | C% | theor. = 43.46 | H% | theor. = 3.16 | N% | theor. = 6.76 |
|---|---|---|---|---|---|---|---|
| | found = 41.58 | | found = 43.28 | | found = 3.13 | | found = 6.23. |

N-methyl-N-(3,3,2-trichloroallyl)-N'-(3,4-dichlorophenyl)urea (mark M 7903); m.p.=105° C.–106° C.:

| Cl% | theor. = 36.45 | H% | theor. = 2.50 | N% | theor. = 7.73 | C% | theor. = 48.91 |
|---|---|---|---|---|---|---|---|
| | found = 36.41 | | found = 2.42 | | found = 7.50 | | found = 48.30. |

N-methyl-N-(3,3-dichloroallyl)-N'-phenylurea (mark M 7568); m.p.=124°–125° C.:

| Cl% | theor. = 27.37 | C% | theor. = 50.98 | H% | theor. = 4.67 | N% | theor. = 10.81 |
|---|---|---|---|---|---|---|---|
| | found = 27.17 | | found = 51.10 | | found = 4.76 | | found = 10.57. |

N-methyl-N-(3,3-dichloroallyl)-N'-(3,4-dichlorophenyl)urea (mark M 7632); m.p.=109°–110° C.:

| Cl% | theor. = 43.24 | C% | theor. = 40.20 | H% | theor. = 3.07 | N% | theor. = 8.54 |
|---|---|---|---|---|---|---|---|
| | found = 42.02 | | found = 40.66 | | found = 3.12 | | found = 8.45. |

N-propargyl-N-(3,3-dichloroallyl)-N'-(4-chlorophenyl)urea (mark M 8122); m.p.=102° C.–103° C.:

| Cl% | theor. = 33.49 | C% | theor. = 49.16 | H% | theor. = 3.49 | N% | theor. = 8.82 |
|---|---|---|---|---|---|---|---|
| | found = 34.73 | | found = 48.94 | | found = 3.45 | | found = 8.80. |

N-ethyl-N-(3,3-dichloroallyl)-N'-(m-chlorophenyl)urea (mark M 8073); m.p.=104°-105°:

Cl% { theor. = 34.58 / found = 35.63 }   C% { theor. = 46.86 / found = 45.19 }   H% { theor. = 4.26 / found = 3.74 }   N% { theor. = 9.11 / found = 9.54. }

N-(1,1-dimethylpropargyl)-N-(3,3,2-trichloroallyl)-N'-(p-chlorophenyl)urea (mark M 8429); m.p.=130°-131° C.:

Cl% { theor. = 37.31 / found = 35.22 }   C% { theor. = 47.40 / found = 47.40 }   H% { theor. = 3.71 / found = 3.74 }   N% { theor. = 7.37 / found = 6.76. }

N-propargyl-N-(3,3,2-trichloroallyl)-N'-(2-trifluoromethylphenyl)urea (mark M 8277); m.p.=70°-71° C.:

Cl% { theor. = 27.59 / found = 26.57. }

EXAMPLE 35

Anti-parasite activity of the compounds of the invention

The compounds of this invention were tested on the larvae of the following insects, using the procedures indicated:

*Pieris brassicae* (lepidoptera)

Small cauliflower plants, grown in pots, were sprinkled with an aqueous dispersion of the products of the invention, at the concentrations indicated in Table I.

After drying, the plants were infected with larvae of 3rd age. The percent mortality (untreated plants: 0% mortality) was assessed 7 days after the treatment.

*Leptinotarsa decemlineata* (coleoptera)

Potato seedlings, grown in pots, were sprinkled with an aqueous dispersion of the products of the invention, at concentrations as indicated in Table I.

After drying, the seedlings were infected with larvae of 3rd age. The percent mortality (untreated plants: mortality 0%), was assessed 7 days after the treatment.

*Aedes aegypti* (diptera)

Amounts of tap water were uniformly mixed with acetone solution of the products of the invention and thereafter were infested with 4 days old larvae regularly supplied with a suitable nourishment.

The number of emerged adults and the mortality, in comparison with the larvae placed in untreated water, were determined every 2 or 3 days until the end of the emergence of the larvae kept as witnesses (controls).

The results obtained are recorded in Table I.

TABLE I

Compound:

$$\text{C}_6\text{H}_4(R)\text{-N(H)-C(O)-N(R}^1\text{)-CH}_2\text{-C(X)=CCl}_2$$

% mortality on larvae at the indicated doses.

| Reference No. | R | $R^1$ | X | PIERIS B. dose: 1% | LEPTINOTARSA D. 1% | LEPTINOTARSA D. 2 ppm | AEDES AEG. 0.2 ppm |
|---|---|---|---|---|---|---|---|
| 7962 | 3,4-di-Cl | H | H | 100 | 100 | 100 | 100 |
| 7635 | 2-F | $CH_3$ | H | 100 | 100 | 8 | |
| 8071 | 4-Cl | $C_2H_5$ | H | 100 | 100 | | |
| 7784 | 3,4-di Cl | $C_2H_5$ | H | 100 | 100 | 100 | |
| 7860 | 2-F | $i\text{-}C_3H_5$ | H | 100 | 100 | 31 | |
| 8076 | 4-Cl | $i\text{-}C_3H_7$ | H | 100 | 100 | | |
| 7859 | 3,4-di Cl | $i\text{-}C_3H_7$ | H | 100 | 100 | | |
| 7857 | 3,4-di Cl | $C_6H_5$ | H | 75 | 100 | 100 | |
| 8079 | 4-di Cl | $CH_2\text{-}CH=CH_2$ | H | 100 | 100 | 100 | |
| 8078 | 3-Cl | $CH_2\text{-}CH=CH_2$ | H | 100 | 100 | 100 | |
| 7718 | 3,4-di Cl | $CH_2\text{-}CH=CH_2$ | H | 100 | 100 | 100 | |
| 7723 | 2-$CF_3$ | $CH_2\text{-}CH=CH_2$ | H | 90 | 100 | | |
| 7721 | 3-Me | $CH_2\text{-}CH=CH_2$ | H | 20 | 100 | | |
| 8273 | 4-Cl | $C(CH_3)_2C\equiv CH$ | H | 100 | 90 | | |
| 7644 | H | $CH_2\text{-}C\equiv CH$ | H | 100 | 100 | 27 | |
| 8122 | 4-Cl | $CH_2\text{-}C\equiv CH$ | H | 100 | 80 | 100 | |
| 7719 | 3,4-di Cl | $CH_2\equiv CH$ | H | 100 | 100 | | 100 |
| 8082 | 3,4-di Cl | H | Cl | 90 | 80 | | |
| 8074 | 4-Cl | $CH_3$ | Cl | 100 | 100 | | |
| 7903 | 3,4-di Cl | $CH_3$ | Cl | 75 | 90 | 100 | |
| 8278 | 3-Cl | $CH_2\text{-}C\equiv CH$ | Cl | 100 | 100 | | |
| 8276 | 4-Cl | $CH_2\text{-}C\equiv CH$ | Cl | 100 | 100 | | |
| 8275 | 3,4-di Cl | $CH_2\text{-}C\equiv CH$ | Cl | 100 | 90 | 100 | |
| 8277 | 2-$CF_3$ | $CH_2\text{-}C\equiv CH$ | Cl | 100 | 100 | | |
| "Dimylin" [1-(4-chlorophenyl)-3-(2,6-difluorobenzoyl)urea], reference product. | | | | 100 | 47 | 100 | |

EXAMPLE 36

Biological activity on *Meloidogyne incognita* (nematoda)

A 1:1 mixture of field earth and sand infested by newborn larvae and eggs of the nematode was treated by mixing with a hydroacetonic dispersion (acetone 20% vol.) in a concentration of 0.1% and 0.02% of the compounds under examination, so as to get soil samples containing 100 ppm and 20 ppm, respectively, of active principle.

The soil was then distributed in plastic pots and after 5 days, 5 small 15 cm high tomato plants were transplanted into each of the pots. 14 days after the transplanting, the plants were extracted and their roots were observed in order to verify the degree of infestation by counting the galls that had formed.

The nematocide activity in Table II is expressed as the percent reduction of the infestation with respect to the witness (small plants transplanted into the same oil treated with a dispersion but without active substance).

TABLE II

Percentage reduction of infestation of nematoda on tomato plants grown on a soil containing 100 ppm, 20 ppm and 4 ppm, respectively, of active substance.

| Compound | Formula | Reduction of infestation 100 ppm | 20 ppm |
|---|---|---|---|
| M 8073 | Cl-C6H4-NH—CO—N(C2H5)CH2—CH=CCl2 | 100 | 100 |
| M 8080 | Cl-C6H4-NH—CO—N(CH2—CH=CH2)2 | 100 | 0 |
| M 8081 | Cl-C6H4-NH—CO—N(CH2—CH=CH2)2 | 100 | 0 |
| M 8129 | CH2=CH—CH2—NH—CO—NH—C6H3Cl2 | 100 | 0 |
| Dichlorodymylin | | 0 | — |

What is claimed is:

1. Method for protecting useful agrarian plants against infestations by the insect parasites coleoptera, diptera, lepidoptera, and by nematodes, which consists in spreading on the plants quantities of at least 0.2 parts per million of a compound of general formula

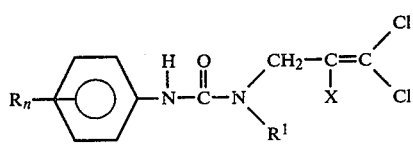

in which:
R is H, halogen, methyl, ethyl or trifluoromethyl;
$R^1$ is H, $C_1$-$C_3$ alkyl, allyl, mono-chloroallyl, di-chloroallyl, propargyl, mono-methyl propargyl, dimethyl-propargyl or phenyl;
n=1 or 2, and
X is H or Cl.

2. The method of claim 1, in which the compund spread on the plants is N-(3,3-dichloroallyl)-N'-(3,4-dichlorophenyl) urea.

3. The method of claim 1, in which the compound spread on the plants is N-methyl-N-(3,3-dichloroallyl)-N'-(2-fluorophenyl) urea.

4. The method of claim 1, in which the compound spread on the plants is N-ethyl-N-(3,3-dichloroallyl)-N'-(4-chlorophenyl) urea.

5. The method of claim 1, in which the compound spread on the plants is N-ethyl-N-(3,3-dichloroallyl)-N'-(3,4-dichlorophenyl) urea.

6. The method of claim 1, in which the compound spread on the plants is N-isopropyl-N-(3,3-dichloroallyl)-N'-(2-fluorophenyl) urea.

7. The method of claim 1, in which the compound spread on the plants is N-isopropyl-N-(3,3-dichloroallyl)-N'-(4-chlorophenyl) urea.

8. The method of claim 1, in which the compound spread on the plants is N-isopropyl-N-(3,3-dichloroallyl)-N'-(3,4-dichlorophenyl) urea.

9. The method of claim 1, in which the compound spread on the plants is N-phenyl-N-(3,3-dichloroallyl)-N'-(3,4-dichlorophenyl) urea.

10. The method of claim 1, in which the compound spread on the plants is N-allyl-N-(3,3-dichloroallyl)-N'-(4-chlorophenyl) urea.

11. The method of claim 1, in which the compound spread on the plants is N-allyl-N-(3,3-dichloroallyl)-N'-(m-chlorophenyl) urea.

12. The method of claim 1, in which the compound spread on the plants is N-allyl-N-(3,3-dichloroallyl)-N'-(3,4-dichlorophenyl) urea.

13. The method of claim 1, in which the compound spread on the plants is N-allyl-N-(3,3-dichloroallyl)-N'-(2-trifluoromethyl-phenyl) urea.

14. The method of claim 1, in which the compound spread on the plants is N-allyl-N-(3,3-dichloroallyl)-N'-(m-methylphenyl) urea.

15. The method of claim 1, in which the compound spread on the plants is N-(3,3-dichloroallyl)-N'-(1,1-dimethylpropargyl)-N'-(p-chlorophenyl) urea.

16. The method of claim 1, in which the compound spread on the plants is N-propargyl-N-(3,3-dichloroallyl)-N'-phenylurea.

17. The method of claim 1, in which the compound spread on the plants is N-propargyl-N-(3,3-dichloroallyl)-N'-(4-chlorophenyl) urea.

18. The method of claim 1, in which the compound spread on the plants is N-propargyl-N-(3,3-dichloroallyl)-N'-(3,4-dichlorophenyl) urea.

19. The method of claim 1, in which the compound spread on the plants is N-methyl-N-(3,3-2-trichloroallyl)-N'-(p-chlorophenyl) urea.

20. The method of claim 1, in which the compound spread on the plants is N-propargyl-N-(3,3,2-trichloroallyl)-N'-(m-chlorophenyl) urea.

21. The method of claim 1, in which the compound spread on the plants is N-propargyl-N-(3,3,2-trichloroallyl)-N'-(p-chlorophenyl) urea.

22. The method of claim 1, in which the compound spread on the plants is N-propargyl-N-(3,3,2-trichloroallyl)-N'-(3,4-dichlorophenyl) urea.

23. The method of claim 1, in which the compound spread on the plants is N-propargyl-N-(3,3,2-trichloroallyl)-N'-(2-trifluoromethyl-phenyl) urea.

* * * * *